United States Patent [19]

Vorwerk

[11] Patent Number: 4,675,457

[45] Date of Patent: Jun. 23, 1987

[54] PROCESS FOR THE PREPARATION OF 4,4′-DIHYDROXYDIPHENYL ETHER

[75] Inventor: Edgar Vorwerk, Frankfurt am Main, Fed. Rep. of Germany

[73] Assignee: Hoechst Aktiengesellschaft, Fed. Rep. of Germany

[21] Appl. No.: 906,995

[22] Filed: Sep. 12, 1986

[30] Foreign Application Priority Data

Sep. 14, 1985 [DE] Fed. Rep. of Germany ....... 3532881

[51] Int. Cl.$^4$ .................... C07C 41/09; C07C 41/40; C07C 43/295
[52] U.S. Cl. .................................................. 568/638
[58] Field of Search ........................................ 568/638

[56] References Cited

U.S. PATENT DOCUMENTS 2,739,171  3/1956  Linn .
3,236,809  2/1966  Goldberg et al. .
3,290,386  12/1966  Stamatoff ............................ 568/638
3,375,297  3/1968  Barth et al. .
3,886,218  5/1975  Biller et al. ........................ 568/638

FOREIGN PATENT DOCUMENTS 1236197  9/1967  Fed. Rep. of Germany .
2237762  2/1974  Fed. Rep. of Germany .

*Primary Examiner*—Bernard Helfin
*Attorney, Agent, or Firm*—Connolly and Hutz

[57] ABSTRACT

The invention relates to a process for the preparation of 4,4′-dihydroxydiphenyl ether by dehydration of hydroquinone using sulfonic acids or sulfuric acid as catalysts at elevated temperatures. The dehydration product is stirred with an excess of water at 80° to 110° C. The higher condensed byproducts which are undissolved during this are separated off, and the ether desired is allowed to crystallize out of the filtrate obtained.

3 Claims, No Drawings

PROCESS FOR THE PREPARATION OF 4,4'-DIHYDROXYDIPHENYL ETHER

The invention relates to a process for the preparation of 4,4'-dihydroxydiphenyl ether by dehydration of hydroquinone using sulfonic acids or sulfuric acid as catalysts at elevated temperatures.

The preparation of 4,4'-dihydroxydiphenyl ether from hydroquinone under dehydrating conditions has already been described many times.

According to U.S. Pat. No. 2,739,171, the dehydration of hydroquinone is preferably carried out in the presence of 95-100% strength hydrofluoric acid, but phosphoric acid, calcium phosphates and acid-reacting oxides or oxide mixtures of silicon, aluminum, zirconium and magnesium are also mentioned as dehydrating agents. The disadvantage is the conversions of only 30% with only a 47% selectivity toward 4,4'-dihydroxydiphenyl ether. A method for the separation of the ether from the byproducts is not specified.

The use of natural or synthetic aluminum silicates (montmorillonite, bentonite) activated with acids for the dehydration of hydroquinone is described in German Offenlegungsschrift No. 2,237,762. A relatively large amount of catalyst is used, which is between 10 and 50% by weight, relative to the hydroquinone employed. The 4,4'-dihydroxydiphenyl ether is separated in a complicated manner, by co-distillation using suitable, high-boiling solvents, from unreacted hydroquinone and higher condensation products from the reaction mixture which is produced.

Finally, it is known from Japanese Published Specification SHO 55/129,237 that 4,4'-dihydroxydiphenyl ether can be prepared from hydroquinone and sulfuric acid or sulfonic acids at elevated temperature. The ether desired is separated from the catalyst, unreacted hydroquinone and higher condensation products by extraction of all the phenolic components using a suitable organic solvent, removal of this solvent, and subsequent distillation of the residue.

The processes described thus provide 4,4'-dihydroxydiphenyl ether in mixtures with unreacted hydroquinone and higher condensed products, the separation of which is complicated and, industrially, not very satisfactory hitherto. The object was therefore to develop a process, for the preparation of the ether mentioned, which is free of these disadvantages. This object is achieved by the present invention.

Accordingly, the invention relates to a process for the preparation of 4,4'-dihydroxydiphenyl ether by dehydration of hydroquinone using sulfonic acids or sulfuric acid as catalysts at elevated temperatures, wherein the dehydration product is stirred with an excess of water at 80°-110° C., the undissolved, higher condensed byproducts are separated, and the ether is allowed to crystallize out from the filtrate.

Aromatic sulfonic acids such as, for example, p-toluenesulfonic acid, benzenesulfonic acid, chlorobenzenesulfonic acid, naphthalene-1-sulfonic acid, naphthalene-2-sulfonic acid, hydroxynaphthalenesulfonic acids and 4-hydroxynaphthalene-2,7-disulfonic acid, are preferably used as catalysts.

The amount of catalyst employed is preferably 1-10% by weight, relative to the hydroquinone.

The dehydration is carried out in the melt, preferably at temperatures of 170°-250° C., particularly 200°-230° C. The reaction duration, measured from the point at which a complete melt was first present, is, in general, several minutes to several hours, preferably 30 min to 1.5 hours.

The water of reaction produced is preferably expelled using an inert gas stream, preferably nitrogen, helium or carbon dioxide. However, the water of reaction can alternatively be removed from the reaction mixture via a descending condenser, inert gas being unnecessary. To separate the reaction product from unreacted hydroquinone, higher condensed byproducts and the catalyst, the reaction mixture, still hot and liquid, is stirred into water and heated to at least 80° C. The upper limit for the temperature is, of course, determined by the boiling point of this mixture, and is in general at about 110° C. The amount of water is, in general, 5 to 50 times the amount by weight of hydroquinone, preferably 8-20 times.

The addition of activated charcoal can be advantageous, but is not necessary.

The higher condensed byproducts remain undissolved during the treatment with water, and are separated, for example by filtration or centrifuging.

The 4,4'-dihydroxydiphenyl ether is precipitated by cooling of the filtrate or centrifugate, preferably to temperatures of 0° C.–40° C., and is isolated by filtration or centrifuging.

Unreacted hydroquinone can be obtained by concentration of the filtrate or centrifugate of this crystallization, and can be recycled.

The process can be carried out continuously or in batches.

The 4,4'-dihydroxydiphenyl ether is an important, bifunctional component in polycondensations and polyadditions. The final products produced from these can be used as insulation material or as thermally stable polymers (German Pat. No. 1,236,197, U.S. Pat. No. 3,375,297 and U.S. Pat. No. 3,236,809).

EXAMPLE 165.2 g (1.5 mol) of hydroquinone and 5 g of p-toluenesulfonic acid monohydrate were mixed in a reaction vessel and kept in an oil bath which was preheated to 210° C. After the reaction mixture had melted completely, it was heated at 210° C. for a further 45 minutes. The water of reaction liberated during the reaction was removed using a stream of nitrogen via a descending condenser.

The liquid reaction mixture, which was still hot, was stirred into 2.5 liters of water and subsequently heated to boiling for 45 minutes, 8 g of activated charcoal being added. The mixture was filtered while hot and the insoluble, higher condensed components of the reaction mixture were separated in this fashion, the filtration being simplified by the use of filtration auxiliaries. The 4,4'-dihydroxydiphenyl ether crystallized out on cooling of the filtrate to 15° C. and was filtered off under suction and isolated.

39.0 g of 4,4'-dihydroxydiphenyl ether, or 36.8 g after recrystallization from xylene, of melting point 163°–165° C. were obtained (yield: 40.7%, relative to converted hydroquinone).

The mother liquor was concentrated. The residue was taken up in acetone and boiled with about 8 g of activated charcoal. 66.64 g of hydroquinone were recovered, contaminated with about 2% of 4,4'-dihydroxydiphenyl ether.

I claim:

1. A process for the preparation of 4,4'-dihydroxydiphenyl ether by dehydration of hydroquinone using sulfonic acids or sulfuric acid as catalysts at elevated temperatures, which comprises stirring the dehydration product with an excess of water at 80°–110° C., separating the undissolved, higher condensed byproducts, and allowing the ether to crystallize out of the filtrate.

2. The process as claimed in claim 1, wherein the amount of water is 5- to 50-times the amount of hydroquinone employed.

3. The process as claimed in claim 1, wherein the amount of water is 8- to 20-times the amount of hydroquinone employed.

* * * * *